US010842479B2

(12) United States Patent
Allen

(10) Patent No.: US 10,842,479 B2
(45) Date of Patent: Nov. 24, 2020

(54) ADJUSTABLE SUTURE RESTRICTION SYSTEM AND METHOD

(71) Applicant: Boston Scientific Scimed, Inc., Maple Grove, MN (US)

(72) Inventor: John J. Allen, Mendota Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 192 days.

(21) Appl. No.: 15/621,425

(22) Filed: Jun. 13, 2017

(65) Prior Publication Data

US 2017/0273682 A1    Sep. 28, 2017

Related U.S. Application Data

(63) Continuation of application No. 14/061,580, filed on Oct. 23, 2013, now Pat. No. 9,706,985.

(60) Provisional application No. 61/717,317, filed on Oct. 23, 2012.

(51) Int. Cl.
*A61B 17/04* (2006.01)
*A61B 17/00* (2006.01)

(52) U.S. Cl.
CPC ...... *A61B 17/0401* (2013.01); *A61B 17/0487* (2013.01); *A61B 2017/00805* (2013.01); *A61B 2017/0404* (2013.01); *A61B 2017/0474* (2013.01)

(58) Field of Classification Search
CPC ........ A61B 17/0401; A61B 2017/0404; A61B 17/0487; A61B 2017/0408; A61B 2017/0474; A61B 2017/0496; Y10T 24/3913; Y10T 24/3969; Y10T 24/3993; F16G 11/108
See application file for complete search history.

(56) References Cited

U.S. PATENT DOCUMENTS

| | | |
|---|---|---|
| 2005/0192632 A1 | 9/2005 | Geissler et al. |
| 2005/0288711 A1 | 12/2005 | Fallin et al. |
| 2007/0073299 A1 | 3/2007 | Dreyfuss et al. |
| 2009/0118776 A1* | 5/2009 | Kelsch ............... A61B 17/0401 606/325 |
| 2013/0123841 A1 | 5/2013 | Lyon et al. |

* cited by examiner

*Primary Examiner* — Wade Miles
(74) *Attorney, Agent, or Firm* — Brake Hughes Bellermann LLP

(57) ABSTRACT

A one-way knot pusher and/or locking device is provided and can be used for the adjustment of soft tissue anchoring components that create or improve continence. The device can be generally button- or disc-shaped and can include a carrier and a pin. When the device is pushed in the free sliding direction it acts as a knot pusher. However, when reversed the suture (e.g., the knot) jams or wedges inside of the cavity of the carrier, restricting or preventing motion in the opposite direction.

18 Claims, 5 Drawing Sheets

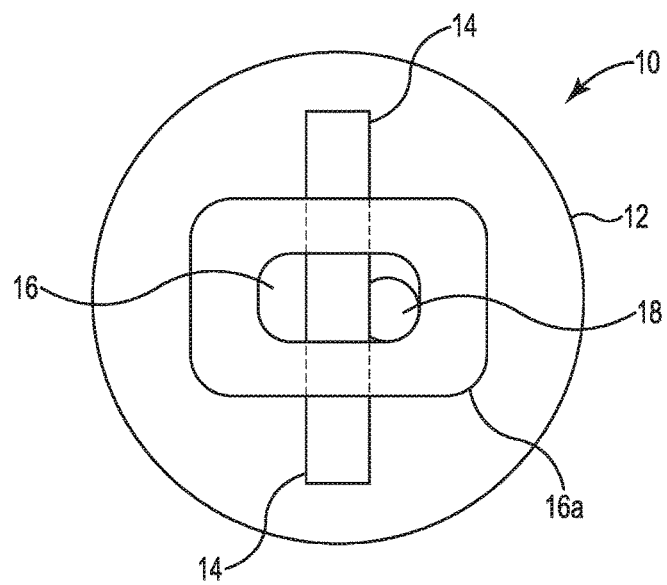
Fig. 2
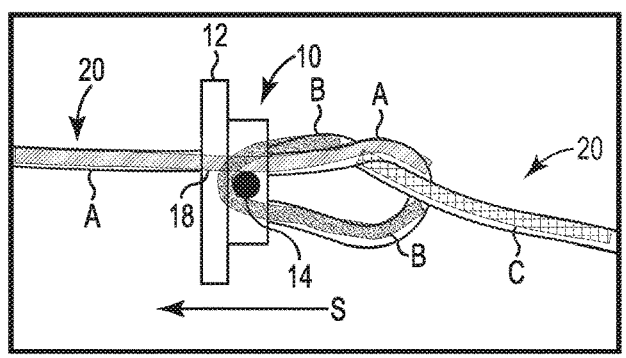 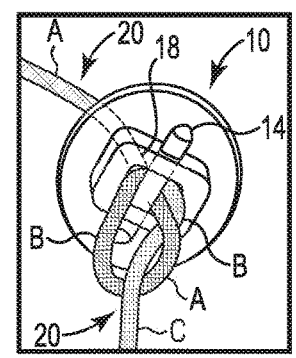
Fig. 3               Fig. 4

ADJUSTABLE SUTURE RESTRICTION SYSTEM AND METHOD

CROSS-REFERENCE TO RELATED APPLICATIONS

This application is a Continuation of, and claims priority to, U.S. patent application Ser. No. 14/061,580, filed on Oct. 23, 2013, entitled "ADJUSTABLE SUTURE RESTRICTION SYSTEM AND METHOD", which, in turn, claims priority to U.S. Patent Application No. 61/717,317, filed on Oct. 23, 2012, the disclosures of which are incorporated by reference herein in their entirety.

FIELD OF THE INVENTION

The present invention relates to apparatus, tools and methods for treating pelvic conditions and, more particularly, an adjustable suture restriction system utilized to advance a component or part attached to a surgical suture.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. The urethra is the tube that passes urine from the bladder out of the body. The narrow, internal opening of the urethra within the bladder is the bladder neck. In this region, the bladder's bundled muscular fibers transition into a sphincteric striated muscle called the internal sphincter. The urethra extends from the bladder neck to the end of the penis. The male urethra is composed of three portions: the prostatic, bulbar and pendulus portions. The prostatic portion is the widest part of the tube, which passes through the prostate gland. The rectum is the most distal portion of the gastrointestinal tract. The exterior opening of the rectum is the anus. Fecal continence is related to control of the exterior sphincter and interior sphincter of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder," "frequency/urgency syndrome," or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. Mid-urethral slings have been effective. One type of procedure, found to be an especially successful treatment option for SUI in both men and women, is a sling and support procedure.

Fecal incontinence, like urinary incontinence, has proven to be challenging to treat. Patients whose fecal incontinence is caused by external anal sphincter injury is treated surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic gracilloplasty, artificial sphincter procedures, and sacral nerve stimulate on. Success has been limited, and the various treatment modalities can result in morbidity.

There is a desire for a minimally invasive yet highly effective treatment modality, tools and devices that can be used with minimal to no side effects for the treatment of both urinary and fecal incontinence.

SUMMARY OF THE INVENTION

The present invention can include surgical instruments, implantable articles, and methods for urological applications, particularly for the treatment of stress and/or urge urinary incontinence, fecal incontinence, and prolapse by implanting a paraurethral or other constraining or support device.

A one-way knot pusher device can be included to advance, e.g., in a single direction, a component or part attached to a suture or like member. This device can be useful for the adjustment of soft tissue anchoring components that support pelvic tissue to create continence. It can also be useful for any number of other applications where one-way tensioning is desired such as anchoring pelvic floor repair meshes for incontinence, prolapse, or hernias. The device can also be used for wound closure and orthopedic procedures such as muscle and tendon repairs. The one-way knot pusher device is advantageous in that it can be constructed as a very small part yet still provide high retention strength.

In one embodiment, the one-way knot pusher device is generally button-shaped and can be held against or abutting soft tissue to provide adjustable tensioning and support. The device can be constructed of three components: a knot carrier (e.g., clear polycarbonate), a pin member (e.g., stainless steel), and a suture (e.g., 2-0 braided nylon). A cavity is formed 15 inside the carrier that is sized such that a suture passing through a suture aperture in the cavity can wrap around the pin for subsequent tying into an overhand knot.

The suture enters the aperture at the face of the device that is toward the free sliding direction, loops around the pin (e.g., into the aperture and under and around pin), and then is twisted through the suture loop. Other types of knots can also be employed with the lock 20 device. When the device is pushed in the free sliding direction it acts as a knot pusher. However, when reversed the suture (e.g., the knot) jams or wedges inside of the cavity of the carrier, restricting or preventing motion in the opposite direction.

Embodiments of the present invention can include apparatus and methods for treating urinary incontinence, fecal incontinence, and other pelvic defects or dysfunctions, in both males and females using one or more implants to reinforce the supportive tissue of the urethra, bladder neck, rectum, etc. The implants can be configured to engage and pull (e.g., pull up) or reposition the supportive tissue, such as the perineal membrane. The perineal membrane is the fibrous membrane in the perineum that intersects the urethra and vagina near the midurethra location and can thus be stabilized or controlled in a manner that helps restore continence. As such, systems, methods and implants can be utilized to eliminate the need for mesh or other supportive structures under the urethra that is common with other incontinence slings. The implants can be shaped to facilitate such support, e.g., provided with anchoring end portions, barbs or other devices of many available shapes and configurations. One or more anchors or tissue engagement portions can be employed to attach and stabilize the implants or devices to tissue.

An anchoring element or portion, such as a medial or proximal anchor, can be fixed on each side of the urethra on the far side of a tissue layer that is known to have relatively high strength and toughness. In certain embodiments, the knot pusher device can also serve as the tissue anchor, while in others it is used in conjunction with a tissue anchor.

A second anchor device, such as a distal anchor or engagement device, can be placed in a lateral or superior position such that a connection between the medial and lateral anchors (via a suture, mesh, wire or like connection) can provide tensile support for the urethra during stress events. The distal anchor device can be fixated to, or around, the tendinous arch of the levator ani (white line), the Cooper's ligament, the obturator foramen, obturator internus, abdominal fascia, sacrospinous ligament, prepubic fascia or muscle, the pubic symphysis cartilage, or other stable anatomical structures.

BRIEF DESCRIPTION OF THE DRAWINGS

FIG. 2 is a top view of a one-way suture knot pusher or locking device, in accordance with embodiments of the present invention.

FIGS. 3-5 are views of a one-way suture knot pusher or locking device deployed along a suture, in accordance with embodiments of the present invention.

DETAILED DESCRIPTION OF PREFERRED EMBODIMENTS

Referring generally to FIGS. 1-7, embodiments of the present invention can include apparatus and methods for treating urinary incontinence, fecal incontinence, and other pelvic defects or dysfunctions, in both males and females using one or more lateral implants to reinforce the supportive tissue of the urethra, bladder neck, rectum, etc.

A one-way knot pusher device is provided and can be used for the adjustment of soft tissue anchoring components that create or improve continence. Further, the knot pusher device can be employed in a number of other applications where one-way tensioning is desired, such as anchoring pelvic floor repair meshes for incontinence, prolapse, or hernias. The device can also be utilized for wound closure and orthopedic procedures, such as muscle and tendon repairs. The device is advantageous in that it is a small component that can provide high retention strength in a wide variety of applications and procedures.

Figure 1:
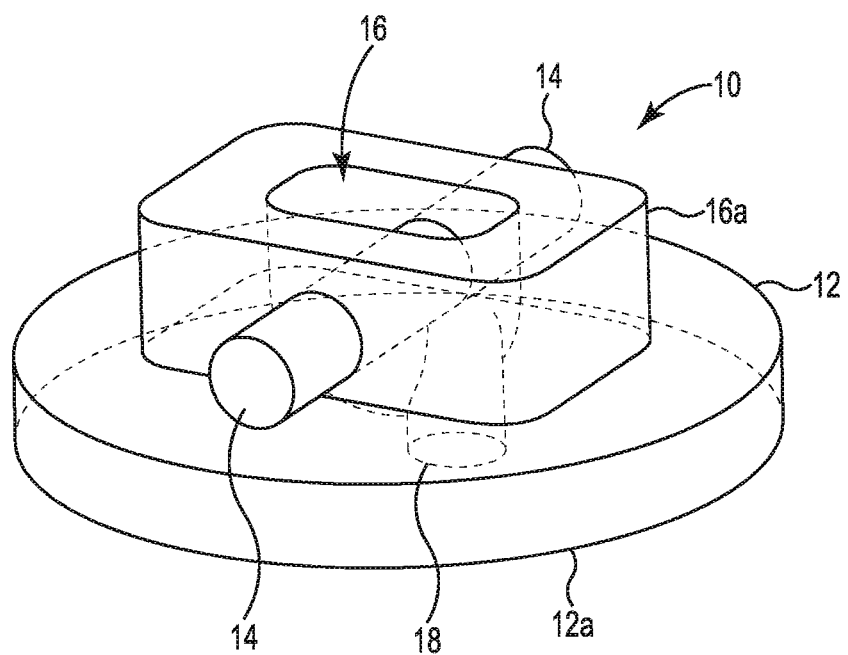
FIG. 1 is a perspective view of a one-way suture knot pusher or locking device, in accordance with embodiments of the present invention.

Referring generally to FIGS. 1-3, the one-way knot or suture lock device 10 can be generally button- or disc-shaped and can include a carrier 12 and a pin 14. In various embodiments, the device 10 or carrier 12 can assume other shapes, including rectangular, oval, square, or a myriad of other shape constructs. The carrier 12 can include a cavity portion 16, and a suture aperture 18 extending therethrough. The aperture 18 can be defined closely adjacent to the pin 14. The pin 14 can be provided to have a level of rotational motion within its confinement in the carrier 12, or the pin 14 can be stationary or fixed.

The cavity portion 16 can be defined in an extending platform 16a, or otherwise defined in a portion of the carrier 12. The cavity 16 is sized and shaped such that a suture passing through from the aperture 18 can wrap around the pin 14 and subsequently be tied into a simple overhand or other acceptable knot configuration. Further, the cavity 16 within the carrier 12 is sized in a manner that facilitates the desired one-way travel. Relative to the center pin 14 diameter, in various embodiments, the clearance around the pin 14 can be approximately one suture width, and axially the space can be approximately two suture widths long. The clearance may be slightly more or less than the described dimensions and proportions depending on the type of suture 20 used and the materials for the pin 14 and carrier 12. Other suture, cavity dimensions and device 10 component configurations and constructs can be employed without deviating from the scope of the present invention, depending on the particular application and procedure requirements.

The suture 20 can follow and engage with the device 10 as shown in FIGS. 3-4. While positions, directions, and like orientations for the suture 20 are depicted with different shadings/hatchings, other configurations and knot constructs can obviously be employed as well to provide the disclosed sliding and locking features of the present invention. The suture 20 enters the aperture 18 at the face 12a of the device 10 that is toward the free sliding direction for segment A, loops around the pin for segment B (e.g., into aperture 16, and under and around pin 14), and then is twisted through the suture loop for segment C. Other types of knots can also be employed with the lock device 10. When the device 10 is pushed in the free sliding direction S it acts as a knot pusher. However, when reversed the suture 20 (e.g., knot 21) jams or wedges inside of the cavity 16 of the carrier 12, preventing motion in the opposite direction.

The carrier 12 can be constructed from nearly any rigid or semi-rigid material including polymers, metals, epoxies, etc. The action of jamming the suture 20 can be accomplished or further facilitated in certain embodiments by incorporating features such as ridges, barbs, surface features, or scales that favor sliding of the suture 20 in one direction and restriction or locking in the opposing direction. Moreover, such features could be added to either the carrier cavity 16 or the center pin 14. The suture 20 can be a braided type material such as nylon or polyester, but the device could also work with monofilament materials.

In certain embodiments, the device 10 can be positioned at the perineal membrane or like anchoring positions at a location near the urethra, or other anchoring spots targeted to treat urinary or fecal incontinence in a patient.

Figure 5:
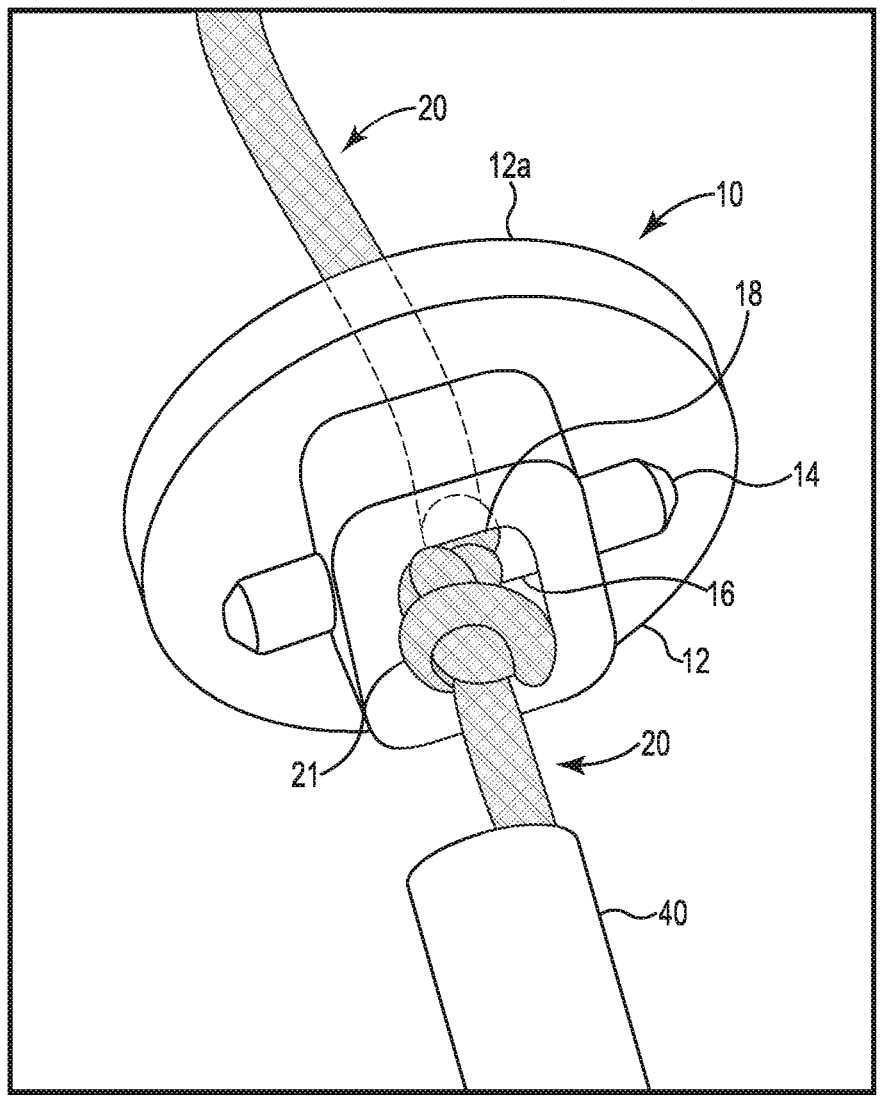
Figure 6:
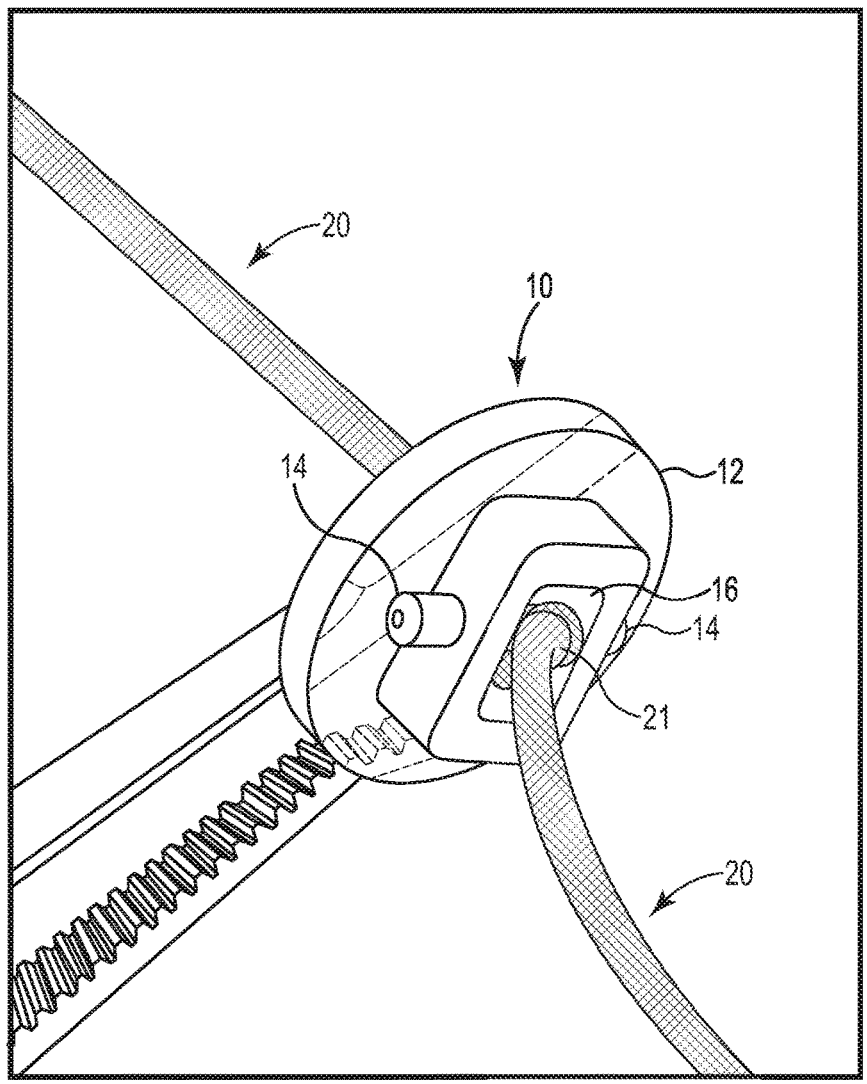
FIG. 6 is a view of a one-way suture knot pusher or locking device deployed along a suture with a knot wedged in a cavity of the device to limit movement in a second direction, in accordance with embodiments of the present invention.

As shown in FIG. 5, a pusher tube 40 can be used to adjust the traction load on the device 10, against tissue, and can then be removed, followed by trimming of the suture 20 to conceal it within the superficial perineal pouch or like anatomical target or anchoring location. FIG. 6 demonstrates the use of a device (e.g., tweezers, needle, scissors, clamp, etc.) in an attempt to reverse the direction of the device 10, with the knot 21 further wedging within the carrier 12 to restrict such movement in a direction opposite the free sliding direction S.

Figure 7:
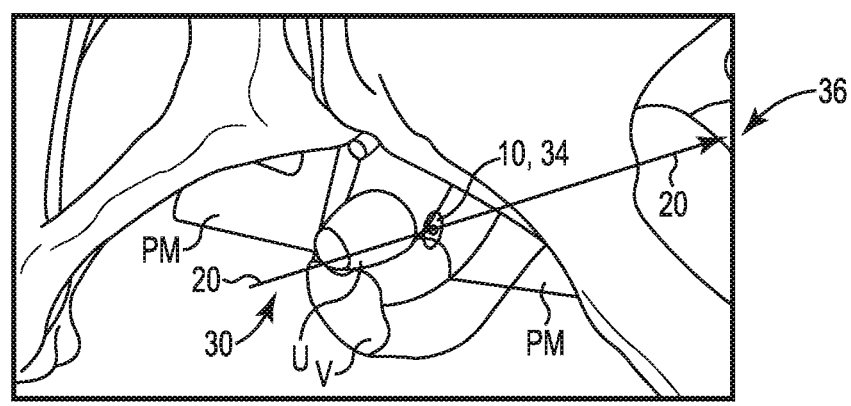
FIG. 7 shows an implant system having a one-way suture knot pusher or locking device deployed within the patient, in accordance with embodiments of the present invention.

An embodiment of the device 10 in use to treat incontinence is shown in FIG. 7. One or more implant devices 30 can be configured to engage and pull (e.g., pull up) or reposition support tissue (e.g., paraurethral), such as the perineal membrane PM, uterovaginal fascia, endopelvic fascia, or other anatomical features at which connective support of the urethra U can be established. The perineal membrane intersects the urethra and vagina V at the midurethra I distal location and can thus be stabilized or controlled in a manner that helps restore continence. As such, the implants can be utilized to eliminate the need for mesh or other supportive structures under the urethra that is common with other incontinence slings. The implants can be shaped to facilitate such support, e.g., provided with anchoring end portions, barbs or other devices of many available shapes, sizes and configurations, and extension members, including those disclosed in U.S. Patent Publication Nos. 2013/0023724, and 2013/0204075, which are incorporated herein by reference in their entireties.

In various embodiments, the one or more implants 30 can be placed in strategically located positions to pull up or otherwise tighten tissue and/or muscle lateral or otherwise intersecting or attached (directly or indirectly) with the urethra to generally stabilize the anatomical structure of the patient. Various systems, devices, structures, techniques and methods, alone or in combination, as disclosed in U.S. Pat. Nos. 7,500,945, 7,407,480, 7,351,197, 7,347,812, 7,303,525, 7,025,063, 6,911,003, 6,691,711, 6,648,921, 6,612,977, 6,802,807, 2002/0161382, 2002/0147382, 2002/151762, 2004/0039453, 2008/0057261, 2008/0045782, 2010/0105979, 2011/0144417, and 2011/0201876 and International PCT Publication Nos. WO 2008/057261 and WO 2007/097994, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

One or more opposing anchors 34, 36 or tissue engagement portions can be employed to attach and stabilize the implants to the tissue, as well as provide selective adjustment. The anchors or engagement portions can be configured to engage soft tissue and can include various barbs, tines, serrated edges, extending fibers, or other similar structural feature to promote tissue fixation. The anchors can be implanted in a direction lateral from the urethra U. The anchors can generally be small enough to be unnoticeable by both the patient and the patient's sexual partner. The anchors and other devices and components of the system may be constructed from various biocompatible materials, such as known polymers and metals that promote long-term resilience, or other materials known to those skilled in the art.

In various embodiments, the lateral or distal anchor devices 36 can be directed for engagement with tissue distal the medial or proximal anchors 34 at target sites such as the obturator foramen, obturator internus muscle, sacrospinous ligament, prepubic fascia or muscle, abdominal fascia, rectus fascia, puboprostatic ligament, the tendinous arch of the levator ani, the Cooper's ligament, and the pubic symphysis.

Various procedural steps or methods can be used to deploy the implant of the present invention. In one embodiment, the device 10 is the medial anchor 34 and is operatively connected to the distal anchor(s) 36 via one or more sutures 20. The device 10 is implanted into tissue, a needle is withdrawn, the lateral (e.g., obturator) anchor 36 is delivered and implanted, and the connecting suture 20 is properly tensioned between the anchors using the one-way knot pusher feature of the device 10 to provide proper support. In other embodiments, the device 10 is used in conjunction with an anchor, such as the medial anchor 34.

The systems, their various components, structures, features, materials and methods of the present invention may have a number of suitable configurations as shown above. Various methods and tools for introducing, deploying, anchoring and manipulating implants or to treat incontinence and prolapse as disclosed in the previously-incorporated references are envisioned for use with the present invention as well.

A variety of materials may be used to form portions or components of the implants and devices, including Nitinol, polymers, elastomers, porous mesh, thermoplastic elastomers, metals, ceramics, springs, wires, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. A surgical suture restriction system, comprising:
   a carrier having a base portion, an extended platform portion defining a cavity, and a pin disposed partially within the cavity, the carrier including a first surface portion and a second surface portion defining a longitudinal line between the first surface portion and the second surface portion, the base portion having a first size being transverse to the longitudinal line, and the extended platform portion having a second size being transverse to the longitudinal line, the second size being smaller than the first size, the base portion including a suture aperture; and a suture insertable through the suture aperture and around the pin within the cavity to define a suture knot, wherein the knot is configured to be disposed within the cavity.

2. The system of claim 1, wherein the pin is fixed.

3. The system of claim 1, wherein the suture knot is an overhand knot.

4. The system of claim 1, wherein the suture is a braided material.

5. The system of claim 1, further including a pusher tube to engage with and slide the carrier in the first direction.

6. The system of claim 1, wherein the carrier is generally disc-shaped.

7. The system of claim 1, wherein the carrier is constructed of a generally rigid polymer material.

8. The system of claim 1, wherein the pin extends through the extended platform portion.

9. The system of claim 8, wherein the base portion is generally cylindrical and the extended platform portion is generally rectangular.

10. The system of claim 1, wherein the carrier is configured to move along a length of the suture in a first direction and the knot is configured to be disposed within the cavity to prevent movement of the carrier along the length of the suture in a second direction, the second direction being opposite the first direction.

11. A surgical anchor and suture restriction system, comprising:

one or more first distal anchors;

a carrier having a base portion, an extended platform portion defining a cavity, and a pin, the pin having a first portion disposed partially within the cavity and a second portion disposed partially outside of the extended platform portion, the base portion including a suture aperture, the carrier including a first surface portion and a second surface portion opposite the first surface portion; and a suture operably connected and extending between the one or more first distal anchors and the carrier, the suture having a first end and a second end opposite the first end, one of the first end or the second end extends through the suture aperture in a first direction at the first surface portion and extends in a second direction, opposite the first direction, at the second surface portion, to define a suture knot, wherein the carrier is configured to move along a length of the suture in a first direction and the knot being configured to be disposed within the cavity to prevent movement of the carrier along the length of the suture in a second direction, the second direction being opposite the first direction.

12. The system of claim 11, wherein the pin is fixed.

13. The system of claim 11, wherein the suture knot is an overhand knot.

14. The system of claim 11, wherein the suture is a braided material.

15. The system of claim 11, further including a pusher tube to engage with and slide the carrier in the first direction.

16. The system of claim 11, wherein the carrier is constructed of a generally rigid polymer material.

17. The system of claim 11, wherein the pin extends through the extended platform portion.

18. The system of claim 17, wherein the base portion is generally cylindrical and the extended platform portion is generally rectangular.

\* \* \* \* \*